United States Patent
Hu

(10) Patent No.: US 7,285,682 B2
(45) Date of Patent: Oct. 23, 2007

(54) TERPHENYL GUANIDINES AS β-SECRETASE INHIBITORS

(75) Inventor: Baihua Hu, Audubon, PA (US)

(73) Assignee: Wyeth, Madison, NJ (US)

( * ) Notice: Subject to any disclaimer, the term of this patent is extended or adjusted under 35 U.S.C. 154(b) by 28 days.

(21) Appl. No.: 11/352,887

(22) Filed: Feb. 13, 2006

(65) Prior Publication Data

US 2006/0183943 A1    Aug. 17, 2006

Related U.S. Application Data

(60) Provisional application No. 60/652,837, filed on Feb. 14, 2005.

(51) Int. Cl.
  *C07C 279/10*    (2006.01)
  *A61K 31/155*    (2006.01)
(52) U.S. Cl. ..................... 564/237; 514/634
(58) Field of Classification Search ............ None
  See application file for complete search history.

(56) References Cited

U.S. PATENT DOCUMENTS 6,399,824 B1    6/2002    Hofmeister et al.

FOREIGN PATENT DOCUMENTS

WO    WO 01/87829 A1    11/2001

*Primary Examiner*—Brian Davis
(74) *Attorney, Agent, or Firm*—Barbara L. Lences

(57) ABSTRACT

The present invention provides terphenyl guanidine compounds of formula I

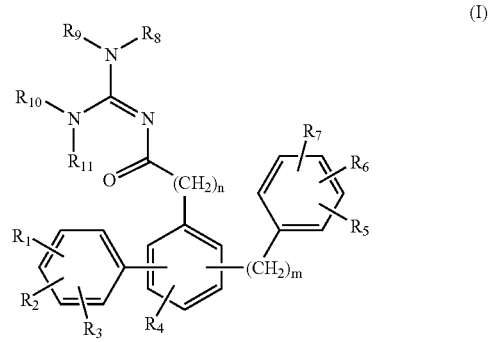

The present invention also provides methods for the use thereof to inhibit β-secretase (BACE) and treat β-amyloid deposits and neurofibrillary tangles.

20 Claims, No Drawings

TERPHENYL GUANIDINES AS β-SECRETASE INHIBITORS

This application claims the benefit under 35 U.S.C. §119 (e) to co-pending U.S. Provisional Application No. 60/652,837, filed Feb. 14, 2005, which is hereby incorporated by reference in its entirety.

BACKGROUND OF THE INVENTION

β-Amyloid deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-Amyloid deposits are predominately an aggregate of Aβ peptide, which in turn is a product of the proteolysis of amyloid precursor protein (APP). More specifically, Aβ peptide results from the cleavage of APP at the C-terminus by one or more β-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a compound of formula I

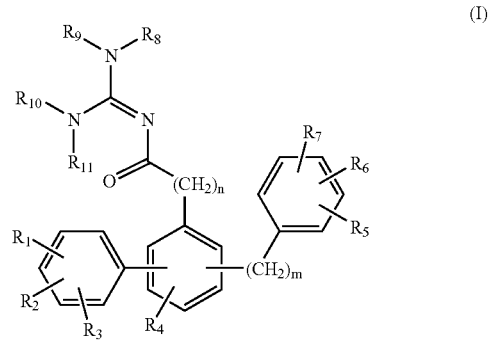

wherein
$R_1$, $R_2$, $R_3$, $R_5$, $R_6$ and $R_7$ are each independently H, halogen, $NO_2$, CN, $OR_{12}$, $COR_{13}$, $COOR_{14}$, $CONR_{15}R_{16}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ and $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl grooup each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;

p is 0, 1 or 2;

$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or a tautomer thereof, a stereoisomer thereof or a pharmaceutically acceptable salt thereof.

The present invention also relates to the use of terphenyl guanidine compounds of formula I for the treatment of β-amyloid deposits and neurofibrillary tangles. These compounds are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that a terphenyl acylguanidine compound of formula I demonstrates inhibition of β-secretase and the selective inhibition of BACE1. Advantageously, said acylguanidine compound may be used as an effective therapeutic agent for the treatment, prevention or amelioration of a disease or disorder characterized by elevated β-amyloid deposits or β-amyloid levels in a patient. Accordingly, the present invention provides a terphenyl acyguanidine compound of formula I

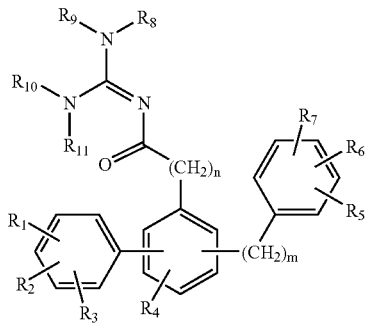

(I)

wherein $R_1$, $R_2$, $R_3$, $R_5$, $R_6$ and $R_7$ are each independently H, halogen, $NO_2$, CN, $OR_{12}$, $COR_{13}$, $COOR_{14}$, $CONR_{15}R_{16}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ and $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl grooup each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;

p is 0, 1 or 2;

$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or a tautomer thereof, a stereoisomer thereof or a pharmaceutically acceptable salt thereof.

Preferred compounds of formula I are those compounds having the structure of formula Ia

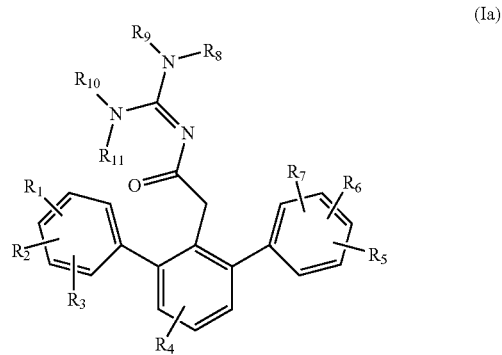

(Ia)

It is understood that the claims encompass all possible stereoisomers, tautomers, and prodrugs. Moreover, unless stated otherwise, each alkyl, alkenyl, alkynyl, cycloalkyl, cycloheteroalkyl, aryl, or heteroaryl is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present.

As used herein, the term "alkyl" includes both ($C_1$-$C_{10}$) straight chain and branched-chain monovalent saturated hydrocarbon moiety. Examples of saturated hydrocarbon alkyl moieties include, but are not limited to, methyl, ethyl, n-propyl, isopropyl, n-butyl, tert-butyl, isobutyl, sec-butyl; n-pentyl, n-hexyl, or the like.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "alkenyl", as used herein, refers to either a ($C_2$-$C_{10}$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, vinyl, 2-propenyl, isopropenyl, crotyl, 2-isopentenyl, butadienyl, 2-(butadienyl), 2,4-pentadienyl, 3-(1,4-pentadienyl), or the like.

The term "cycloalkyl" as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Examples of cycloalkyl moieties include, but are not limited to, cyclopropyl, cyclobutyl, cyclopentyl, cyclohexyl, cycloheptyl, norbornyl, adamantyl, spiro[4.5]decanyl, or the like.

The term "cycloheteroalkyl" as used herein designates a five- to seven-membered cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR, O or S and R is H or an optional substituent as defined hereinbelow.

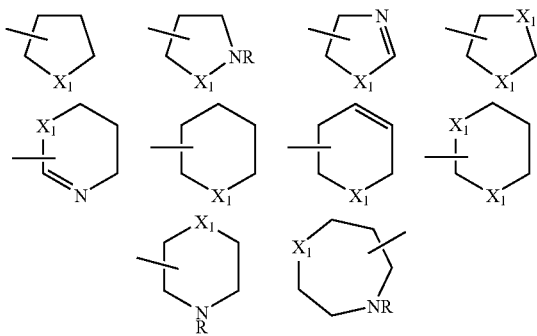

The term "halogen" designates fluorine, chlorine, iodine, and bromine.

The term "aryl", as used herein, refers to an aromatic carbocyclic moiety of up to 20 carbon atoms, which may be a single ring (monocyclic) or multiple rings (bicyclic, up to three rings) fused together or linked covalently. Examples of aryl moieties include, but are not limited to, phenyl, 1-naphthyl, 2-naphthyl, biphenyl, anthryl, phenanthryl, fluorenyl, indanyl, biphenylenyl, acenaphthenyl, acenaphthylenyl, or the like.

The term "heteroaryl", as used herein, refers to an aromatic heterocyclic ring system, which may be a single ring (monocyclic) or multiple rings (bicyclic, up to three rings) fused together or linked covalently. The rings may contain from one to four hetero atoms selected from nitrogen, oxygen, or sulfur, wherein the nitrogen or sulfur atom(s) are optionally oxidized, or the nitrogen atom(s) are optionally quarternized. Examples of heteroaryl moieties include, but are not limited to, furan, thiophene, pyrrole, pyrazole, imidazole, oxazole, isoxazole, thiazole, isothiazole, 1H-tetrazole, 1,3,4-oxadiazole, 1H-1,2,4-triazole, 1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, α-carboline, or the like.

The compounds of the present invention can be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Tautomers often exist in equilibrium with each other. As these tautomers interconvert under environmental and physiological conditions, they provide the same useful biological effects. The present invention encompasses mixtures of such tautomers.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Preferred compounds of formula I are those compounds wherein n is 1 and m is 0. Another group of preferred compounds are those compounds of formula I wherein $R_4$, $R_8$, $R_9$ $R_{10}$ and $R_{11}$, are H. Also preferred are those compounds of formula I having the structure of formula Ia.

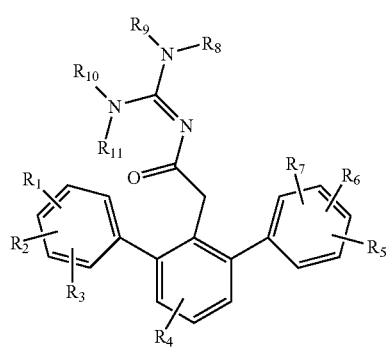

(Ia)

More preferred compounds of the invention are those compounds of formula Ia wherein $R_1$ is H, $C_1$-$C_4$alkyl or phenoxy and $R_2$, $R_3$, $R_4$, $R_5$, $R_6$, and $R_7$ are H. Another group of more preferred compounds of the invention are those compounds of formula Ia wherein R1 and R2 are taken together with the atoms to which they are attached to form a 6-membered aromatic ring and $R_3$, $R_4$, $R_5$, $R_6$, and $R_7$ are H. A further group of more preferred compounds of the invention are those compounds of formula Ia wherein $R_1$ is H, tert-butyl or phenoxy and $R_2$, $R_3$, $R_4$, $R_5$, $R_6$, $R_7$, $R_8$, $R_9$, $R_{10}$ and $R_{11}$ are H.

Preferred compounds of the invention include:
N-(1,1':3',1''-terphenyl-2'-ylacetyl)guanidine;
N-{[3-(2-naphthyl)-1,1'-biphenyl-2-yl]acetyl}guanidine;
N-[(4-tert-butyl-1,1':3',1''-terphenyl-2'-yl)acetyl]guanidine;
N''-[(4-phenoxy-1,1':3',1''-terphenyl-2'-yl)acetyl]guanidine;

the tautomers thereof; the stereoisomers thereof; or the pharmaceutically acceptable salts thereof.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic scheme. The skilled practitioner will know how to make use of variants of these process steps, which in themselves are well known in the art.

For example, compounds of formula I wherein m is 0 and n is 1 (Ib) may be prepared as shown in Scheme 1 below.

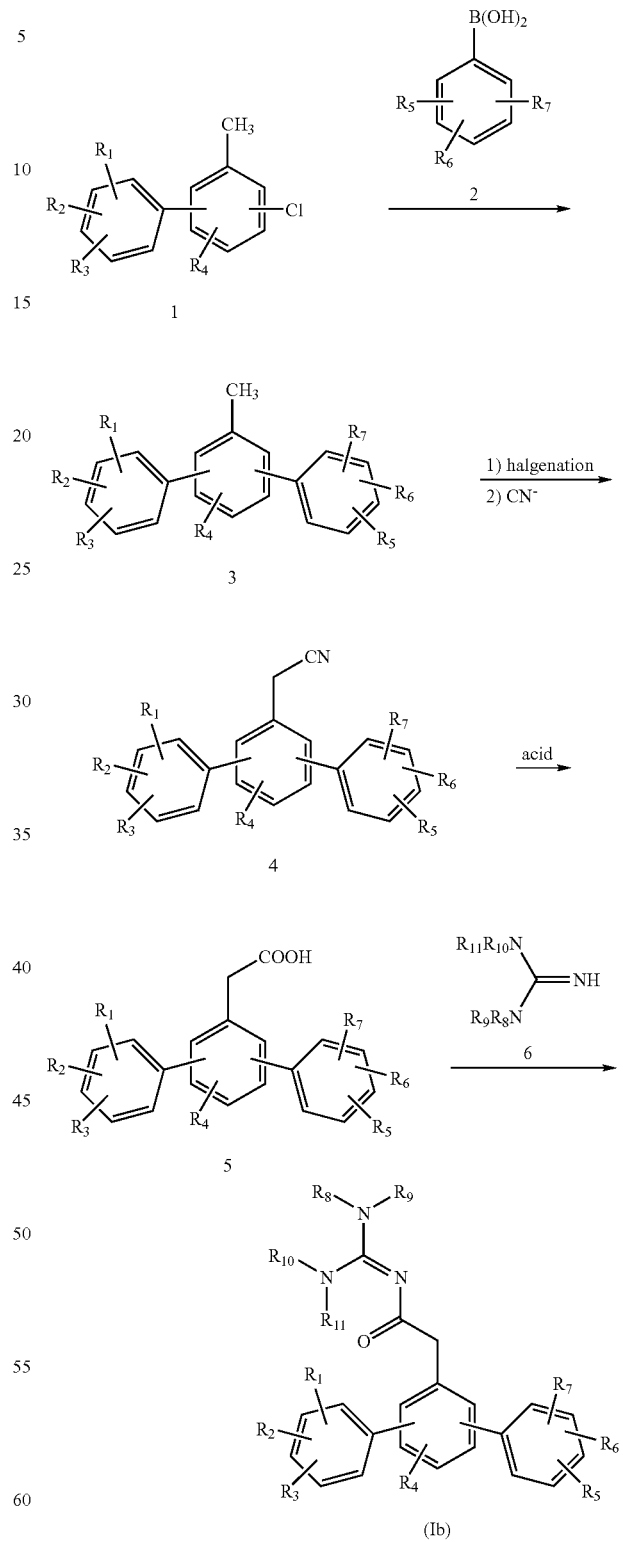

In scheme 1, the chloride 1 and the boronic acid 2 undergo a Suzuki coupling reaction in the presence of a base, such as $Na_2CO_3$, and $Pd(PPh_3)_4$ in an inert solvent such as toluene at 80 to 100° C. to give the intermediate 3. Compound 3 is readily converted to the corresponding phenyl acetonitrile 4 by reacting said comound 3 sequentially with a halogenating agent such as chlorine, bromine, N-chlorosuccinimide, N-bromosuccinimide or the like to give a benzyl halide and treating the benzyl halide with sodium cyanide or potassium cyanide in a polar solvent to produce the phenyl-acetonitrile 4. Said acetonitrile 4 is treated with a strong inorganic acid, such as sulfuric acid, nitric acid, hydrochloric acid or the like to give the carboxylic acid 5. The carboxylic acid 5 is coupled with the subtituted guandine 6 in the presence of a coupling agent such as 1,1'-carbonyldiimidazole, 1,3-dicyclohexylcarbodiimide, 1-[3-(dimethylamino)propyl]-3-ethylcarbodiimide, diisopropylcarbodiimide, 6-chloro-2,4-dimethoxy-1,3,5-triazine or the like and a base such as triethylamine, diisopropylethyl amine, N-methyl morpholine or the like to give the desired compound of formula I wherein n is 1 and m is 0 (Ib).

The present invention also provides methods for treating a patient having a disease or disorder associated with excessive BACE activity which comprises providing to the patient an effective amount of a compound of Formula I. Representative diseases include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides methods for modulating (and, preferably, inhibiting) the activity of BACE, comprising administering to a patient and/or contacting a receptor thereof with an effective amount of at least one compound of Formula I. Certain methods further comprise determining BACE activity, either before or after said contacting step.

The present invention also provides methods of ameliorating amyloid deposits in a mammal, comprising administering to said mammal an effective amount of at least one compound of Formula I. Further methods ameliorate neurofibrillary tangles in a mammal, and comprise administering to said mammal an effective amount of at least one compound of Formula I.

Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal, comprising administering to said mammal an effective amount of at least one compound of Formula I.

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise administering to said mammal an amount of at least one compound of Formula I that is effective to prevent such disease.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition form which the patient is suspected to suffer.

It has been found in accordance with the present invention that these compounds act as BACE inhibitors for the treatment of amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. This invention also provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve administering to a patient suspected of suffering from or being susceptible to the disease or injury an effective amount of a compound of formula I. Also according to the present invention there is provided a method of treating Alzheimer's disease and related senile dementia's in humans or other mammals which comprises administering to a human or other mammal an effective amount of a compound of the present invention.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of formula I and one or more pharmaceutically acceptable carriers.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The present invention also comprises pharmaceutical compositions comprising compounds of the above-described Formula I and a pharmaceutically acceptable carrier.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, e.g., as discussed in, e.g., Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

The present compounds are further described in the following examples. The following abbreviations are used: DMSO is dimethylsulfoxide, DMF is N,N-dimethylformamide, NMR is proton nuclear magnetic resonance, and MS is mass spectroscopy with (+) referring to the positive mode which generally gives a M+1 (or M+H) absorption where M=the molecular mass. All compounds are analyzed at least by MS and NMR.

EXAMPLE 1

Preparation of N-(1,1':3',1"-Terphenyl-2'-ylacetyl) guanidine TFA salt

Step 1

A mixture of 2'-bromomethyl-[1,1':3',1"]terphenyl (Tetrahedron Lett. 42; 5467-5472 (2001)) (1.65 g, 5.1 mmol) and sodium cyanide (0.27 g, 5.6 mmol) in 10 mL of DMF was stirred at room temperature overnight. The reaction mixture was poured into water, extracted with diethyl ether and dried over magnesium sulfate. The solvent was removed and the residue was purified by silica gel chromatography (eluting with 0-4% ethyl acetate in hexane) to give [1,1';3',1"] terphenyl-2'-yl-acetonitrile as a white solid (0.78 g, 57%): MS (ESI) m/z 270.1 (M+H); HRMS calcd for $C_{20}H_{15}N$, 270.1277. Found (ESI+): 270.1274; $^1$H NMR (DMSO-$d_6$): δ 3.57 (s, 2H), 7.20-7.50 (m, 13H).

Step 2

A mixture of [1,1';3',1"]terphenyl-2'-yl-acetonitrile (0.78 g, 2.9 mmol) in 28 mL of 10:3:1 acetic acid/sulfuric acid/water was refluxed for 2 days The reaction mixture was cooled and diluted with water. The aqueous was extracted with diethyl ether, dried over magnesium sulfate and concentrated to give 1,1':3',1"-terphenyl-2'-ylacetic acid as a tan solid (0.64 g, 76%): MS (ESI) m/z 287.1 (M–H); MS (ESI) m/z 575.2 (2M–H); MS (ESI) m/z 333 (M+FA–H); HRMS calcd for $C_{20}H_{16}O_2$, 288.1150. Found (ESI+), 289.12244; $^1$H NMR (DMSO-$d_6$): δ 3.30 (s, 2H), 7.30-7.50 (m, 13H), 12.07 (br s, 1H); Anal. Calcd for $C_{20}H_{16}O_2$: C, 83.31; H, 5.59. Found: C, 83.02; H, 5.35.

Step 3

1,1'-Carbonyldiimidazole (0.39 g, 2.4 mmol) was added to a stirred solution of 1,1':3',1"-terphenyl-2'-ylacetic acid (0.14 g, 0.049 mmol) in DMF at room temperature. After stirring for 2 hours guanidine carbonate (0.88 g, 4.9 mmol) and triethylamine (0.67 mL, 4.9 mmol) were added. The reaction mixture was stirred overnight, diluted with ethyl acetate, washed with water, and concentrated. The residue was purified by semi-preparative HPLC (Column: Phenomenex C18 Luna 21.6 mm×60 mm, 5 μM; Solvent A: Water (0.1% TFA buffer); Solvent B: Acetonitrile (0.1% TFA buffer); Solvent Gradient: Time 0: 0% B; 10 min: 100% B; Hold 100% B 5 min. Flow Rate: 22.5 mL/min). The product was collected based on UV absorption and concentrated to give the title compound as a white solid (0.13 g, 59%): mp 64-67° C.; MS (ESI) m/z 330.1 (M+H); HRMS calcd for $C_{21}H_{19}N_3O.C_2F_3O_2$: 442.1379. Found (ESI+): 330.1598; $^1$H NMR (DMSO-$d_6$): δ 3.61 (s, 2H), 7.20-7.50 (m, 5H), 8.15 (brs, 4H), 11.11 (brs, 1H); Anal. Calcd for $C_{21}H_{19}N_3O.C_2F_3O_2$: C, 62.44; H, 4.33; N, 9.50. Found: C, 61.12; H, 4.46; N, 9.30.

EXAMPLE 2

Preparation of N-{[3-(2-Naphthyl)-1,1'-biphenyl-2-yl]acetyl}guanidine

Step 1

To a mixture of potassium phosphate (8.36 g 40 mmol), palladium acetate (0.88 g, 0.4 mmol), 2-(dicyclohexylphosphino)biphenyl (0.54 g, 1.6 mmol) and nphtalene-2-boronic acid (5.09 g, 30 mmol) was added 3-cloro-2-methyl-biphenyl (4.0 g, 20 mmol). The reaction mixture was heated to 80° C. overnight, diluted with diethyl ether, washed with water and dried over MgSO$_4$. Removal of solvent under reduced pressure gave a crude product that was purified by silica gel chromatography eluting with hexanes gave 2-(2-methyl-1,1'-biphenyl-3-yl)naphthalene as a white solid; mp 106-107° C.; MS (EI) m/z 294.17 (M+); $^1$H NMR (CDCl$_3$): δ 2.15 (s, 3H), 7.20-7.55 (m, 11H), 7.75-7.90 (m, 4H); Anal. Calcd for C$_{23}$H$_{18}$: C, 93.84; H, 6.16. Found: C, 93.81; H, 5.95.

Step 2

A solution of 2-(2-methyl-1,1'-biphenyl-3-yl)naphthalene (2.0 g, 6.8 mmol) and 200 mg of benzoyl peroxide was refluxed, then NBS (1.21 g, 6.8 mmol) was added. The reaction mixture was refluxed overnight, diluted with methylene chloride, washed with water and dried over MgSO$_4$. Removal of solvent under reduced pressure gave a crude product. The crude product was dissolved in 20 mL of DMF and sodium cyanide (0.65 g, 13 mmol) was added. The reaction was stirred at room temperature for 2 hours, diluted with ethyl acetate, washed with water and dried over MgSO$_4$. Removal of solvent under reduced pressure gave a crude product that was purified by silica gel chromatography eluting with 0.4% ethyl acetate/hexanes to give 1.15 g of (3-naphthalen-2-yl-biphenyl-2-yl)-acetonitrile: $^1$H NMR (CDCl$_3$): δ 3.43 (s, 2H), 7.30-7.60 (m, 11H), 7.80-7.95 (m, 4H).

Step 3

(3-Naphthalen-2-yl-biphenyl-2-yl)-acetic acid was prepared from (3-naphthalen-2-yl-biphenyl-2-yl)-acetonitrile followed the procedure of Example 1 Step 2 as a light yellow solid; MS (ESI) m/z 338.2 (M+H); MS (ESI) m/z 675.3 (2M+H); $^1$H NMR (CDCl$_3$): δ 3.41 (s, 2H), 7.20-7.60 (m, 11H), 7.54 (s, 1H), 7.56-8.00 (m, 3H), 12.05 (brs, 1H); HRMS: calcd for C$_{24}$H$_{19}$NO, 337.1467. Found (ESI+), 338.15406; Anal. Calcd for C$_{24}$H$_{19}$NO: C, 85.43; H, 5.68; N, 4.15. Found: C, 85.18; H, 5.50; N, 4.06.

Step 4

Using essentially the same procedure described in Example 1 Step 3 and employing 3-naphthalen-2-yl-biphenyl-2-yl)-acetic acid, the title compound was prepared and isolated as a yellow solid; mp 36.8-36.9° C.; MS (ESI) m/z 380.2 (M+H); MS (ESI) m/z 759.6 (2M+H); $^1$H NMR (DMSO-d$_6$): δ 3.65 (s, 2H), 7.25-7.60 (m, 11H), 7.80-8.00 (m, 4H), 8.15 (brs, 3H), 11.06 (s, 1H); HRMS calcd for C$_{25}$H$_{21}$N$_3$O C$_2$F$_3$O$_2$, 492.1535. Found (ESI+), 380.17536.

EXAMPLE 3

Preparation of N-[(4-tert-Butyl-1,1':3',1"-terphenyl-2'-yl)acetyl]guanidine

Step 1

Using essentially the same procedures described in Example 2 Steps 1 to 3 and employing 3-cloro-2-methyl-biphenyl and 4-tert-butylbenzene boronic acid, 4-tert-butyl-[1,1':3', 1"]terphenyl-2'-yl)-acetic acid was prepared, MS (ESI) m/z 343.3 (M−H); $^1$H NMR (DMSO-d$_6$): δ 1.32 (s, 9H), 3.34 (s, 2H), 7.15-7.45 (m, 12H), 12.08 (brs, 1H); HRMS calcd for C$_{24}$H$_{24}$O$_2$: 345.1849. Found (ESI+), 345.1847.

Step 2

Using essentially the same procedure described in Example 1 Step 3 and employing 4-tert-butyl-[1,1':3',1"] terphenyl-2'-yl)-acetic acid, the title compound was prepared and isolated as a white solid; mp 171-174° C.; MS (ESI) m/z 386.3 (M+H); $^1$H NMR (DMSO-d$_6$): δ 1.31 (s, 9H), 3.62 (s, 2H), 7.20-7.50 (m, 12H), 8.10 (brs, 3H), 11.12 (s, 1H); HRMS calcd for C$_{25}$H$_{27}$N$_3$O 386.2229. Found (ESI+): 386.2223.

EXAMPLE 4

Preparation of N"-[(4-Phenoxy-1,1':3',1"-terphenyl-2'-yl)acetyl]guanidine

Step 1

(4-Phenoxy-1,1':3',1"-terphenyl-2'-yl)acetic acid was prepared from 3-cloro-2-methyl-biphenyl and 4-phenoxyphenyl boronic acid using essentially the same procedures described in Example 2 Steps 1 to 3 and isolated as a white solid: MS (ESI) m/z 444.1 (M+ACN+Na); 761.3 (2M+H); $^1$H NMR (DMSO-d$_6$) δ 2.65 (s, 2H), 7.05-7.55 (m, 17H), 12.10 (s, 1H); HRMS calcd for C$_{26}$H$_{21}$O$_3$: 381.1485. Found (ESI+): 381.1478.

Step 2

Using essentially the same procedure described in Example 1 Step 3 and employing 4-phenoxy-1,1':3',1"-terphenyl-2'-yl)acetic acid, the title compound was prepared and isolated as a white solid; MS (ESI) m/z 422.0 (M+H); 843.3 (2M+H); $^1$H NMR (DMSO-d$_6$): δ 2.65 (s, 2H), 7.00-7.50 (m, 17H), 8.10 (brs, 3H), 11.10 (s, 1H); HRMS calcd for C$_{27}$H$_{24}$N$_3$O$_2$ 422.1863. Found (ESI+): 422.18568.

EXAMPLE 5

Evaluation of BACE-1 Binding Affinity of Test Compounds

1. Fluorescent Kinetic Assays

Final Assay Conditions: 10 nM human BACE1 (or 10 nM Murine BACE1, 1.5 nM human BACE2), 25 µM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24,124-5, CHAPS was from Research Organics, Cat. # 1304C 1x, PBS was from Mediatech (Cellgro), Cat# 21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 µM (1:1000) in 1xPBS. Concentration is determined by absorbance at 354 nm using an extinction coefficient ε of 18172 M$^{-1}$ cm$^{-1}$, the concentration of stock substrate is corrected, and the substrate stock stored in small aliquots in −80° C.

[Substrate Stock]=$ABS^{354\ nm}$*10$^6$/18172 (in mM)

The extinction coefficient $\epsilon^{354\ nm}$ was adapted from TACE peptide substrate, which had the same quencher-fluorophore pair.

Determination of Stock Enzyme Concentration: the stock concentration of each enzyme is determined by absorbance at 280 nm using ε of 64150 M$^{-1}$ cm$^{-1}$ for hBACE1 and MuBACE1, 62870 M$^{-1}$ cm$^{-1}$ for hBACE2 in 6 M Guanidinium Hydrochloride (from Research Organics, Cat. # 5134G-2), pH ~6. The extinction Coefficient $\epsilon^{280}_{nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 µL 2x inhibitor dilutions in buffer A (66.7 mM Na-Acetate, pH 4.5, 0.0667% CHAPS) were prepared, 4x enzyme dilution in buffer A (66.7 mM Na-Acetate, pH 4.5, 0.0667% CHAPS) were prepared, 100 μM substrate dilution in 1×PBS was prepared, and 50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

$$\% \text{ Inhibition}=100*(1-v_i/v_0)$$

$v_i$: substrate cleavage rate in the presence of inhibitor $v_0$: substrate cleavage rate in the absence of inhibitor $IC_{50}$ Determination:

$$\% \text{ Inhibition}=((B*IC_{50}{}^n)+(100*I_0{}^n))/(IC_{50}{}^n+I_0{}^n)$$

(Model # 39 from LSW Tool Bar in Excel where B is the % inhibition from the enzyme control, which should be close to 0.) % Inhibition is plotted vs. Inhibitor Concentration ($I_0$) and the data fit to the above equation to obtain $IC_{50}$ value and Hill number (n) for each compound. Testing at least 10 different inhibitor concentrations is preferred. Results are presented below in Table I.

TABLE I

| Example | $IC_{50}$, μM BACE1 |
|---|---|
| 1 | 15 |
| 2 | 29.6 |
| 3 | 13.9 |
| 4 | 5.95 |

What is claimed is:

1. A compound of formula I

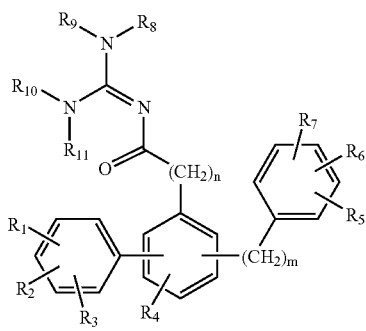

(I)

wherein
$R_1$, $R_2$, $R_3$, $R_5$, $R_6$ and $R_7$ are each independently H, halogen, $NO_2$, CN, $OR_{12}$, $COR_{13}$, $COOR_{14}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ and $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl group each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;

p is 0, 1 or 2;

$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or a tautomer thereof, a stereoisomer thereof or a pharmaceutically acceptable salt thereof.

2. The compound according to claim 1 wherein n is 1 and m is 0.

3. The compound according to claim 1 wherein $R_4$, $R_8$, $R_9$, $R_{10}$ and $R_{11}$ are H.

4. The compound according to claim 1 having the structure of formula Ia

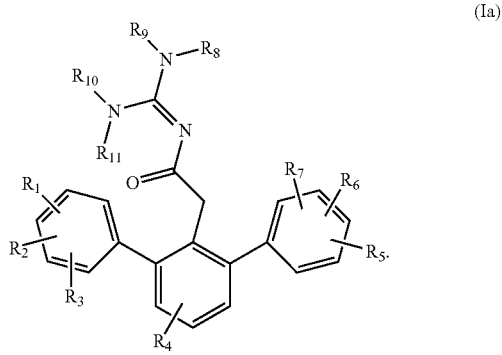

(Ia)

5. The compound according to claim 2 wherein $R_1$ is H, $C_1$-$C_4$alkyl or phenoxy and $R_2$, $R_3$, $R_4$, $R_5$, $R_6$, and $R_7$ are H.

6. The compound according to claim 2 wherein $R_1$ and $R_2$ are taken together with the atoms to which they are attached to form a 6-membered aromatic ring and $R_3$, $R_4$, $R_5$, $R_6$, and $R_7$ are H.

7. The compound according to claim 4 wherein $R_1$ is H, tert-butyl or phenoxy and $R_2$, $R_3$, $R_4$, $R_5$, $R_6$, $R_7$, $R_8$, $R_9$, $R_{10}$ and $R_{11}$ are H.

8. The compound according to claim 4 wherein $R_1$ and $R_2$ are taken together with the atoms to which they are attached to form a 6-membered aromatic ring and $R_3$, $R_4$, $R_5$, $R_6$, and $R_7$ are H.

9. The compound according to claim 4 selected from the group consisting of:

N-(1, 1': 3', 1''-terphenyl-2'-ylacetyl)guanidine;

N-{[3-(2-naphthyl)-1, 1'-biphenyl-2-yl]acetyl}guanidine;

N-[(4-tert-butyl-1, 1':3', 1''-terphenyl-2'-yl)acetyl]guanidine;

N''-[(4-phenoxy-1, 1':3', 1''-terphenyl-2'-yl)acetyl]guanidine;

a tautomer thereof;
a stereoisomer thereof; and
a pharmaceutically acceptable salt thereof.

10. A method for the treatment of a disease or disorder associated with excessive BACE activity in a patient in need thereof which comprises providing to said patient an effective amount of a compound of formula I

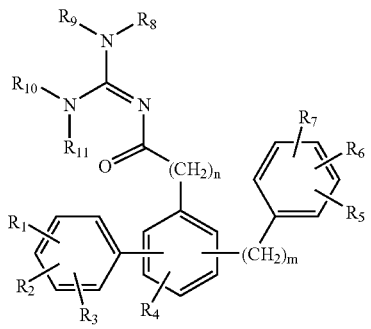

(I)

wherein
$R_1$, $R_2$, $R_3$, $R_5$, $R_6$ and $R_7$ are each independently H, halogen, $NO_2$, CN, $OR_{12}$, $COR_{13}$, $COOR_{14}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ and $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl group each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;
p is 0, 1 or 2;
$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or
a tautomer thereof, a stereoisomer thereof or a pharmaceutically acceptable salt thereof.

11. The method according to claim 10 wherein the disease or disorder is is characterized by production of β-amyloid deposits or neurofibrillary tangles.

12. The method according to claim 10 wherein said disease or disorder is Alzheimer's disease, cognitive impairment, Down's Syndrome, HCHWA-D, cognitive decline, senile dementia, cerebral amyloid angiopathy, or a neurodegenerative disorder.

13. The method according to claim 12 having a formula I compound wherein said compound has the structure of formula Ia

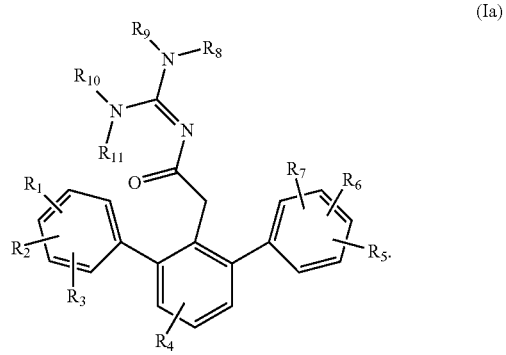

(Ia)

14. A method for modulating the activity of BACE which comprises contacting a receptor thereof with an effective amount of a compound of formula I

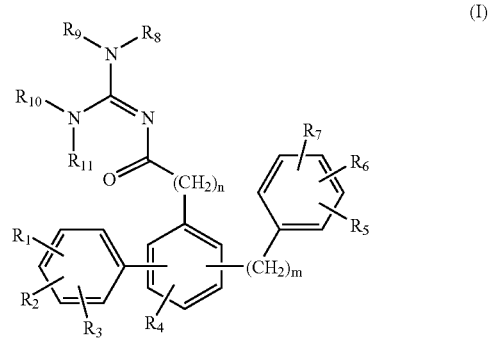

(I)

wherein
$R_1$, $R_2$, $R_3$, $R_5$, $R_6$ and $R_7$ are each independently H, halogen, $NO_2$, CN, $OR_{12}$, $COR_{13}$, $COOR_{14}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ and $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl group each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;
p is 0, 1 or 2;
$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or a tautomer thereof, a stereoisomer thereof or a pharmaceutically acceptable salt thereof.

15. A pharmaceutical composition which comprises a pharmaceutically acceptable carrier and an effective amount of a compound of formula I

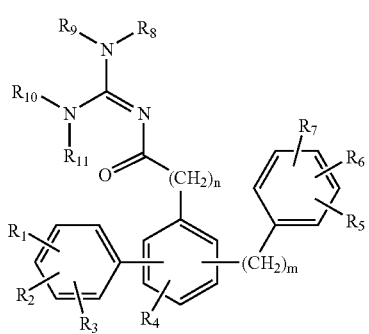

(I)

wherein $R_1$, $R_2$, $R_3$, $R_5$, $R_6$ and $R_7$ are each independently H, halogen, $NO_2$, CN, $OR_{12}$, $COR_{13}$, $COOR_{14}$, $SO_pR_{17}$, $NR_{18}COR_{19}$, $NR_{20}R_{21}$, or an alkyl, haloalkyl, alkenyl, alkynyl, cycloheteroalkyl, aryl or heteroaryl group each group optionally substituted or when attached to adjacent carbon atoms $R_1$ and $R_2$ or $R_5$ $R_6$ may be taken together with the atoms to which they are attached to form a 5- to 6-membered aromatic ring optionally containing one or two heteroatoms selected from N, O or S;

$R_4$, $R_8$, $R_9$, $R_{10}$ and $R_{11}$ are each independently H or an alkyl, aryl, arlyalkyl, cycloalkyl, cycloheteroalkyl or heteroaryl group each group optionally substituted or $R_8$ and $R_9$ or $R_{10}$ and $R_{11}$ may be taken together with the atom to which they are attached to form a 5- to a 7-membered ring optionally containing an additional heteroatom selected from N, O or S;

m and n are each independently 0, 1, 2, 3, 4, 5 or 6;

p is 0, 1 or 2;

$R_{12}$, $R_{13}$, $R_{14}$, and $R_{19}$ are each independently H or an alkyl, haloalkyl, alkenyl, alkynyl, cycloalkyl, cycloheteroalkyl, aryl or heteroaryl group each group optionally substituted;

$R_{17}$ is $NR_{20}R_{21}$ or an alkyl, alkenyl, alkynyl, cycloalkyl, cycloheteroalkyl, aryl or heteroaryl group each group optionally substituted; and $R_{18}$, $R_{20}$, and $R_{21}$ are each independently H or an alkyl, alkenyl or cycloalkyl grop each group optionally substituted or $R_{20}$ and $R_{21}$ may be taken together with the atom to which they are attached to form a 5- to a 7-membered ring optionally containing an additional heteroatom selected from N, O or S; or a tautomer thereof, a stereoisomer thereof or a pharmaceutically acceptable salt thereof.

16. The composition according to claim 15 having a formula I compound wherein n is 1 and m is 0.

17. The composition according to claim 15 having a formula I compound wherein said compound has the structure of formula Ia

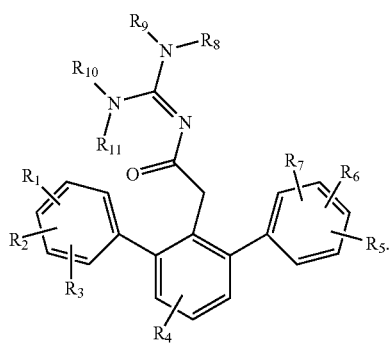

(Ia)

18. The composition according to claim 17 having a formula Ia compound wherein $R_1$ is H, tert-butyl or phenoxy and $R_2$, $R_3$, $R_4$, $R_5$, $R_6$, $R_7$, $R_8$, $R_9$, $R_{10}$ and $R_{11}$ are H.

19. The composition according to claim 17 having a formula Ia compound wherein $R_1$ and $R_2$ are taken together with the atoms to which they are attached to form a 6-membered aromatic ring and $R_3$, $R_4$, $R_5$, $R_6$, and $R_7$ are H.

20. The composition according to claim 15 having a formula I compound selected from the group consisting essentially of:

N-(1, 1':3', 1"-terphenyl-2-ylacetyl)guanidine;

N-{[3-(2-naphthyl)-1, 1'-biphenyl-2-yl]acetyl}guanidine:

N-[(4-tert-butyl-1, 1':3', 1"-terphenyl-2'-yl)acetyl]guanidine;

N"-[(4-phenoxy-1, 1':3', 1"-terphenyl-2'-yl)acetyl]guanidine;

a tautomer thereof;

a stereoisomer thereof; and a pharmaceutically acceptable salt thereof.

* * * * *